(12) United States Patent
Bonfanti et al.

(10) Patent No.: US 8,178,694 B2
(45) Date of Patent: May 15, 2012

(54) HETEROCYCLYLAMINOALKYL SUBSTITUTED BENZIMIDAZOLES

(75) Inventors: Jean-François Bonfanti, Andé (FR); Philippe Muller, Andé (FR); Jérôme Michel Claude Fortin, Igoville (FR); Frédéric Marc Maurice Doublet, Isneauville (FR)

(73) Assignee: Tibotec Pharmaceuticals Ltd. (IE)

( * ) Notice: Subject to any disclaimer, the term of this patent is extended or adjusted under 35 U.S.C. 154(b) by 1181 days.

(21) Appl. No.: 11/993,126

(22) PCT Filed: Jun. 20, 2006

(86) PCT No.: PCT/EP2006/063366
§ 371 (c)(1),
(2), (4) Date: Dec. 19, 2007

(87) PCT Pub. No.: WO2006/136562
PCT Pub. Date: Dec. 28, 2006

(65) Prior Publication Data
US 2010/0272683 A1    Oct. 28, 2010

(30) Foreign Application Priority Data
Jun. 20, 2005 (EP) .................................. 05076439

(51) Int. Cl.
*A61K 31/5377* (2006.01)
*C07D 413/14* (2006.01)

(52) U.S. Cl. .................. 548/307.4; 514/234.5; 514/395; 514/388; 544/124; 544/139; 548/306.1

(58) Field of Classification Search ................ 548/307.4
See application file for complete search history.

(56) References Cited

U.S. PATENT DOCUMENTS
2003/0187258 A1* 10/2003 Swayze et al. ................ 544/184

FOREIGN PATENT DOCUMENTS
| WO | WO 01/00611 A | 1/2001 |
|---|---|---|
| WO | WO 01/00612 A2 | 1/2001 |
| WO | WO 01/00615 A | 1/2001 |
| WO | WO 01/95910 | 12/2001 |
| WO | WO 02/092575 A | 11/2002 |
| WO | WO 2005/058871 A | 6/2005 |
| WO | WO 2005/058874 A | 6/2005 |

* cited by examiner

*Primary Examiner* — Laura L. Stockton
(74) *Attorney, Agent, or Firm* — Mary A. Appollina

(57) ABSTRACT

Heterocyclylaminoalkyl Substituted Benzimidazoles Inhibitors of RSV replication of formula (I): The salts and stereochemically isomeric forms thereof, wherein Q is hydrogen, C1-6alkyl optionally substituted with a heterocycle or Q is C1-6alkyl substituted with both —OR4 and a heterocycle; wherein said heterocycle is oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine, pyrrolidine, piperidine, homopiperidine, piperazine; which heterocycle may be substituted with 1-2 substituents; each Alk is C1-6alkanediyl; R1 is Ar or optionally substituted piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazo lyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl or 2,3-dihydro-1,4-dioxino[2,3-b]pyridyl; R3 is hydroxyC1-6alkyl, C1-6alkoxyC1-6alkyl, cyanoC1-6alkyl, aminocarbonyl-C1-6-alkyl, mono- or di(C1-6alkyl)aminocarbonyl-C1-6-alkyl, carboxyl-C1-6-alkyl, C1-6alkoxycarbonyl-C1-6 alkyl; R2, R4 and R5 are hydrogen or C1-6alkyl; Het is pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazo lyl, benzthiazolyl, pyridopyridyl, naphthiridinyl, 1H-imidazo[4,5-b]-pyridinyl, 3H-imidazo[4,5-b]pyridinyl, imidazo[1,2-a]pyridinyl and 2,3-dihydro-1,4-dioxino[2,3-b]pyridyl; Ar is optionally substituted phenyl; pharmaceutical compositions containing compounds (I) and processes for preparing compounds (I).

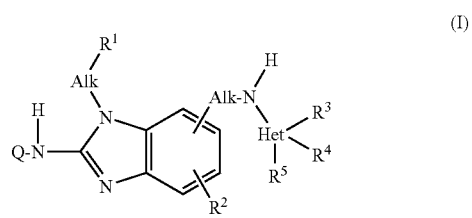

(I)

15 Claims, No Drawings

HETEROCYCLYLAMINOALKYL SUBSTITUTED BENZIMIDAZOLES

This application is a National Stage application under 35 U.S.C. 371 of PCT International Application No. PCT/EP2006/063366, filed Jun. 20, 2006, which claims priority from European Patent Application No. EP 05076439.8, filed Jun. 20, 2005, the contents of which are hereby incorporated by reference.

The present invention is concerned with 1-[2-amino-3-(substituted alkyl)-3H-benzimidazolylmethyl]-3-substituted-1,3-dihydro-benzoimidazol-2-ones and structural analogs having inhibitory activity on the replication of the respiratory syncytial virus (RSV). It further concerns compositions comprising these compounds as active ingredient as well as processes for preparing these compounds and compositions.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Reinfection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Groups of benzimidazoles and imidazopyridines have been described in WO-01/00611, WO-01/00612 and WO-01/00615 as inhibitors of RSV replication. The compounds of the present invention differ from these prior art compounds both in terms of chemical structure and activity profile.

The present invention concerns inhibitors of RSV replication, which can be represented by formula (I)

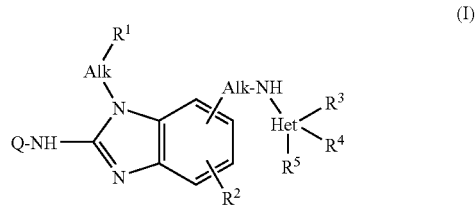

the salts and stereochemically isomeric forms thereof, wherein

Q is hydrogen, $C_{1-6}$alkyl optionally substituted with a heterocycle or Q is $C_{1-6}$alkyl substituted with both a radical —$OR^6$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine, pyrrolidine, piperidine, homopiperidine, piperazine; wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-6}$alkyloxycarbonyl, aminocarbonyl, mono- or di($C_{1-6}$alkyl)aminocarbonyl, $C_{1-6}$alkylcarbonylamino, aminosulfonyl and mono- or di($C_{1-6}$alkyl)aminosulfonyl;

each Alk independently represents $C_{1-6}$alkanediyl;

$R^1$ is Ar or a heterocycle selected from pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]-pyridinyl, imidazo[1,2-a]pyridinyl and 2,3-dihydro-1,4-dioxino [2,3-b]pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$alkyloxy, ($C_{1-6}$alkyloxy)$C_{1-6}$alkyloxy, $C_{1-6}$alkylthio, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl, aminocarbonyl, mono- and di-$C_{1-6}$ alkylaminocarbonyl;

$R^2$ is hydrogen or $C_{1-6}$alkyl;

$R^3$ is hydroxy$C_{1-6}$alkyl, $C_{1-6}$alkoxy$C_{1-6}$alkyl, cyano$C_{1-6}$alkyl, aminocarbonyl-$C_{1-6}$-alkyl, mono- or di($C_{1-6}$alkyl)aminocarbonyl-$C_{1-6}$-alkyl, carboxyl-$C_{1-6}$-alkyl, $C_{1-6}$alkoxycarbonyl-$C_{1-6}$alkyl;

$R^4$ is hydrogen or $C_{1-6}$alkyl;

$R^5$ is hydrogen or $C_{1-6}$alkyl;

Ar is phenyl or phenyl substituted with 1 to 5, such as 1, 2, 3 or 4, substituents selected from halo, hydroxy, amino, mono- or di($C_{1-6}$alkyl)amino, $C_{1-6}$alkylcarbonylamino, $C_{1-6}$alkylsulfonylamino, cyano, $C_{1-6}$alkyl, $C_{2-6}$alkenyl, $C_{2-6}$alkynyl, phenyl, hydroxy$C_{1-6}$alkyl, polyhalo$C_{1-6}$ alkyl, amino$C_{1-6}$alkyl, mono- or di($C_{1-6}$alkyl)amino$C_{1-6}$ alkyl, $C_{1-6}$alkyloxy, polyhalo$C_{1-6}$alkyloxy, phenoxy, aminocarbonyl, mono- or di($C_{1-6}$alkyl)aminocarbonyl, hydroxycarbonyl, $C_{1-6}$alkoxycarbonyl, $C_{1-6}$alkylcarbonyl, aminosulfonyl, mono- and di($C_{1-6}$alkyl)aminosulfonyl;

Het is a heterocycle selected from the group consisting of pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl.

The invention also relates to the use of a compound of formula (I), or an addition salt and stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or an addition salt and stereochemically isomeric form thereof.

As used in the foregoing and hereinafter, 'polyhalo$C_{1-6}$ alkyl' as a group or part of a group, e.g. in polyhalo$C_{1-6}$ alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-4}$alkyl, the halogen atoms may be the same or different.

Each Ar may be unsubstituted phenyl or phenyl substituted with 1 to 5 substituents, such as 5 or 4 substituents or, which is preferred, up to 3 substituents, or up to two substituents, or with one substituent.

A hydroxy$C_{1-6}$alkyl group when substituted on an oxygen atom or a nitrogen atom preferably is a hydroxy$C_{2-6}$alkyl group wherein the hydroxy group and the oxygen or nitrogen are separated by at least two carbon atoms.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of formula (I), their addition salts and stereochemically isomeric forms.

Some of the compounds of formula (I) may contain one or more centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their salts and solvates, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "compounds of formula (I)", or any similar terms such as "compounds of the invention" and the like, is meant to also comprise any prodrugs that the compounds of formula (I) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-7}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Alkanoyl esters for example are any $C_{1-30}$alkanoyl esters, in particular $C_{8-30}$alkanoyl esters, more in particular $C_{10-24}$alkanoyl esters, further in particular $C_{16-20}$alkanoyl esters, wherein the alkyl part may have one or more double bonds. Examples of alkanoyl esters are decanoate, palmitate and stearate.

The term "compounds of formula (I)", or any similar terms such as "compounds of the invention" and the like, is meant to also comprise any metabolites that are formed in vivo upon administration of the drug. Some examples of metabolites in accordance with the invention include, but are not limited to, (a) where the compound of formula (I) contains a methyl group, a hydroxymethyl derivative thereof; (b) where the compound of formula (I) contains an alkoxy group, an hydroxy derivative thereof; (c) where the compound of formula (I) contains a tertiary amino group, a secondary amino derivative thereof; (d) where the compound of formula (I) contains a secondary amino group, a primary derivative thereof; (e) where the compound of formula (I) contains a phenyl moiety, a phenol derivative thereof; and (f) where the compound of formula (I) contains an amide group, a carboxylic acid derivative thereof.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

The term "compounds of formula (I)", or any similar terms such as "compounds of the invention" and the like, is meant to also comprise quaternary amines which are the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyl iodide or benzyl iodide. Other reactants with good leaving groups may also be used, such as alkyl trifluoromethanesulfonates, alkyl methanesulfonates, and alkyl p-toluenesulfonates. A quaternary amine has a positive charged nitrogen. Pharmaceutically acceptable counter ions include chloro, bromo, iodo, trifluoroacetate and acetate. The counter ion of choice can be introduced using ion exchange resins.

The term "compounds of formula (I)", or any similar terms such as "compounds of the invention" and the like, is meant to also comprise the metal complexes or metal chelates thereof wherein the complex or chelate is derived from physiologically acceptable metal ions such as Ca, Zn, Mg or Fe ions. Such metal complex or chelate derivatives of the compounds of formula (I) can be obtained by reacting a compound of formula (I) with a metal salt.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention.

One embodiment of the present invention concerns compounds of formula (I-a):

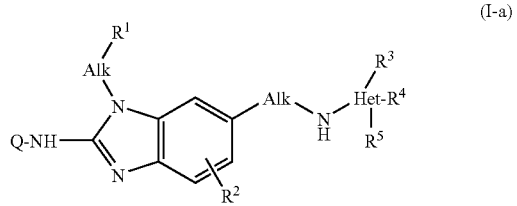

(I-a)

Another embodiment of the present invention concerns compounds of formula (I-b):

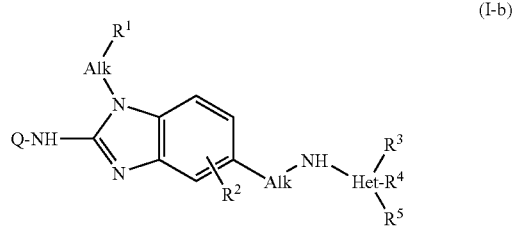

(I-b)

In (I-a) and (I-b) Q, Alk, $R^2$, $R^3$, $R^4$, $R^5$ are as specified in the definitions of the compounds of formula (I) or of any of the subgroups of compounds of formula (I) specified herein.

It is to be understood that the above defined subgroups of compounds of formulae (I-a) or (I-b) as well as any other subgroup defined herein, are meant to also comprise any addition salts and stereochemically isomeric forms of such compounds.

A number of subgroups of compounds of formula (I) are specified hereafter by restricted definitions of the various radicals in the compounds of formula (I). These subgroups however are also meant to comprise those with any permutation of the restricted definitions mentioned hereinafter.

Subgroups I of the compounds of formula (I) are those compounds of formula (I), or any subgroup of compounds of formula (I) specified herein, wherein one or both of the radicals Alk is ethylene or methylene, more in particular wherein one or both of the radicals Alk is methylene.

Subgroups II of the compounds of formula (I) are those compounds of formula (I), or any subgroup of compounds of formula (I) specified herein, such as the subgroups I mentioned above, wherein (a) $R^1$ is Ar or a heterocycle selected from pyridyl, pyrazinyl, pyridazinyl, pyrimidinyl, furanyl, thienyl, pyrrolyl, thiazolyl, oxazolyl, imidazolyl, isothiazolyl, pyrazolyl, isoxazolyl, quinolinyl, benzofuranyl, benzimidazolyl, benzoxazolyl, benzthiazolyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyloxycarbonyl, aminocarbonyl, mono- and di-$C_{1-6}$alkylaminocarbonyl;

(b) $R^1$ is Ar, or a heterocycle selected from quinolinyl, benzimidazolyl, pyrazinyl or pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyloxycarbonyl, aminocarbonyl, mono- and di-$C_{1-6}$ alkylaminocarbonyl;

(c) $R^1$ is Ar, quinolinyl, benzimidazolyl, pyrazinyl or pyridyl, wherein each of these radicals may optionally be substituted with one, two or three radicals selected from the group consisting of halo, hydroxy, $C_{1-6}$alkyl, $C_{1-6}$alkyloxy;

(d) $R^1$ is phenyl optionally substituted with one, two or three radicals selected from the group consisting of halo, hydroxy, $C_{1-6}$alkyl, $C_{1-6}$alkyloxy; quinolinyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i); or wherein (e) $R^1$ is phenyl optionally substituted with one or two radicals selected from the group consisting of halo, hydroxy, $C_{1-6}$alkyl, $C_{1-6}$alkyloxy;

(f) $R^1$ is pyrazinyl optionally substituted with up to three radicals selected from $C_{1-6}$alkyl.

(g) $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-6}$alkyloxy)$C_{1-6}$alkyloxy;

(h) $R^1$ is pyridyl substituted with 1 or 2 substituents independently selected from the group consisting of hydroxy, $C_{1-6}$alkyl, halo and $C_{1-6}$alkyloxy;

(i) $R^1$ is pyridyl substituted with 1 or 2 substituents independently selected from the group consisting of hydroxy and $C_{1-6}$alkyl; or (j) $R^1$ is pyridyl substituted with hydroxy and $C_{1-6}$alkyl.

Embodiments of the invention are compounds of formula (I) or any of the subgroups of compounds of formula (I) wherein Alk is methylene and $R^1$ is as specified above in (a)-(j).

Subgroups III of the compounds of formula (I) are those compounds of formula (I), or any subgroup of compounds of formula (I) specified herein, such as the subgroups I and II mentioned above, wherein $R^2$ is hydrogen.

Further embodiments of the invention are compounds of formula (I) or any of the subgroups of compounds of formula (I) wherein (a) $R^3$ is hydroxy$C_{1-6}$alkyl, $C_{1-6}$alkoxy$C_{1-6}$alkyl or cyano$C_{1-6}$alkyl; or (b) $R^3$ is hydroxy$C_{1-6}$alkyl.

Subgroups IV of the compounds of formula (I) are those compounds of formula (I), or any subgroup of compounds of formula (I) specified herein, such as the subgroups I, II and III mentioned above, wherein $R^4$ is hydrogen.

Subgroups V of the compounds of formula (I) are those compounds of formula (I), or any subgroup of compounds of formula (I) specified herein, such as the subgroups I, II, III and IV mentioned above, wherein $R^5$ is hydrogen.

Subgroups VI of the compounds of formula (I) are those compounds of formula (I), or any subgroup of compounds of formula (I) specified herein, such as the subgroups I, II, III, IV and V mentioned above, wherein (a) Q is hydrogen or $C_{1-6}$alkyl optionally substituted with a heterocycle or Q is $C_{1-6}$alkyl substituted with both a radical —$OR^6$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine; wherein each of said heterocyle may be optionally substituted with one or two substituents selected from the group consisting of $C_{1-6}$alkyl, hydroxy$C_{1-6}$alkyl, hydroxy, carboxyl, $C_{1-6}$alkyloxycarbonyl, aminocarbonyl;

(b) Q is hydrogen or $C_{1-6}$alkyl optionally substituted with a heterocycle or Q is $C_{1-6}$alkyl substituted with both a radical —$OR^6$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl; wherein each of said heterocyle may be optionally substituted with one or two substituents selected from the group consisting of $C_{1-6}$alkyl, hydroxy$C_{1-6}$alkyl, hydroxy;

(c) Q is hydrogen or $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, morpholinyl, thiomorpholinyl; wherein each of said heterocyle may be optionally substituted with one or two $C_{1-6}$alkyl radicals;

(d) Q is $C_{1-6}$alkyl substituted with morpholinyl or thiomorpholinyl.

Preferably in (a)-(d) in the previous paragraph the heterocycles such as oxazolidine, thiazolidine, 1-oxo-thiazolidine, 1,1-dioxothiazolidine, morpholinyl, thiomorpholinyl, etc., are linked by their nitrogen atom to the $C_{1-6}$alkyl on which they are substituted.

Embodiments of the invention are those compounds of formula (I) or compounds belonging to any of the subgroups of compounds of formula (I) specified herein, wherein Ar is phenyl or phenyl substituted with 1, 2, 3 substituents or with 1, 2 substituents selected from those mentioned in the definition of the compounds of formula (I) or of any subgroup thereof.

Subgroups VII of the compounds of formula (I) are those compounds of formula (I), or any subgroup of compounds of formula (I) specified herein, such as the subgroups I, II, III, IV, V and VI mentioned above, wherein:

(a) Ar is phenyl or phenyl substituted with up to 3 substituents, or with up to 2 substituents, or with one substituent, selected from the group consisting of halo, hydroxy, amino, cyano, $C_{1-6}$alkyl, hydroxy$C_{1-6}$alkyl, polyhalo$C_{1-6}$alkyl, amino$C_{1-6}$alkyl, $C_{1-6}$alkyloxy, aminosulfonyl, aminocarbonyl, hydroxycarbonyl, $C_{1-4}$alkylcarbonyl, mono- or di($C_{1-4}$alkyl)amino and $C_{1-4}$alkoxycarbonyl; or (b) Ar is phenyl or phenyl substituted with up to 3 substituents, or with up to 2 substituents, or with one substituent, selected from the group consisting of halo, hydroxy, amino, cyano, $C_{1-6}$alkyl, trifluoromethyl, $C_{1-6}$alkyloxy, mono- and di($C_{1-4}$alkyl)amino; or (c) Ar is phenyl or phenyl substituted with up to 3 substituents, or with up to 2 substituents, or with one substituent, selected from halo, hydroxy, $C_{1-6}$alkyl, hydroxy$C_{1-6}$alkyl, trifluormethyl, and $C_{1-6}$alkyloxy; or (d) Ar is phenyl or phenyl substituted with up to 3 substituents, or with up to 2 substituents, or with one substituent, selected from the group consisting of halo, hydroxy, $C_{1-6}$alkyl, trifluoromethyl and $C_{1-6}$alkyloxy; or (e) Ar is phenyl or phenyl substituted with up to 3 substituents, or with up to 2 substituents, or with one substituent, selected from halo, hydroxy, $C_{1-6}$alkyl and $C_{1-6}$alkyloxy; or (f) Ar is phenyl or phenyl substituted with up to 3 substituents, or with up to 2 substituents, or with one substituent, selected from halo and $C_{1-6}$alkyl.

Subgroups VIII of the compounds of formula (I) are those compounds of formula (I), or any subgroup of compounds of formula (I) specified herein, such as the subgroups I, II, III, IV, V, VI and VII mentioned above, wherein (a) Het is pyridyl, pyrazinyl, pyrimidinyl, furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzimidazolyl, benzoxazolyl, benzthiazolyl;

(b) Het is pyridyl, pyrazinyl, pyrimidinyl, furanyl, thienyl, thiazolyl, oxazolyl;

(c) Het is pyridyl, pyrazinyl, pyrimidinyl, furanyl, thienyl;

(d) Het is pyridyl, pyrazinyl, pyrimidinyl;

(e) Het is pyridyl.

The compounds of formula (I) or any of the subgroups thereof can be prepared as in the following reaction schemes.

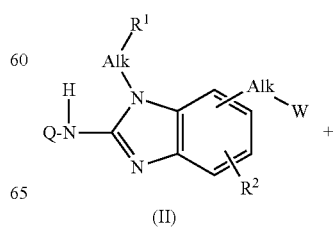

(II)

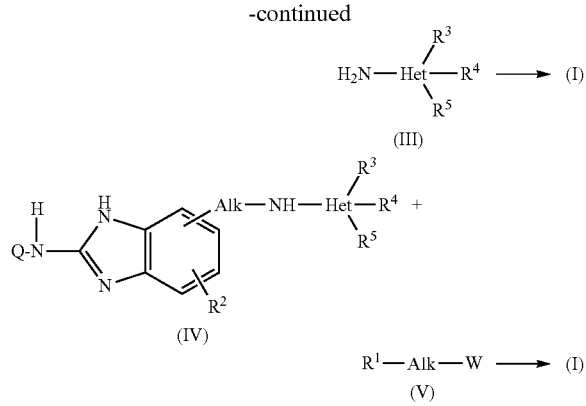

In these schemes Q, each Alk, $R^1$, $R^2$, $R^3$, $R^4$, $R^5$ have the meanings defined above for the compounds of formula (I) or of any of the subgroups thereof. W is an appropriate leaving group, such as tosylate, mesylate or halo, preferably it is chloro or bromo. The reactions of these schemes may be conducted in a suitable solvent in the presence of a base such as an alkali metal carbonate or hydroxide, e.g. sodium, potassium or cesium carbonate; or an organic base such as a trialkylamine, e.g. triethylamine. Suitable solvents for this reaction are for example ethers, e.g. THF, dioxane; halogenated hydrocarbons, e.g. dichoromethane, $CHCl_3$, toluene, polar aprotic solvents such as DMF, DMSO, DMA and the like.

The compounds of formula (I) can also be prepared via a reductive amination process starting from an aldehyde or ketone of formula (VI) wherein Alk' has the same meaning of the radical Alk, but lacks one hydrogen atom. The intermediate (VI) is reacted with the heterocyclylamine (III) in the presence of a reducing agent such as hydrogen in the presence of a noble metal catalyst or a hydride such as a borohydride, e.g. sodium cyanoborohydride. The reductive amination reaction preferably is conducted in a suitable solvent such as an alcohol, e.g. methanol or ethanol, or an ether, e.g. THF or dioxane.

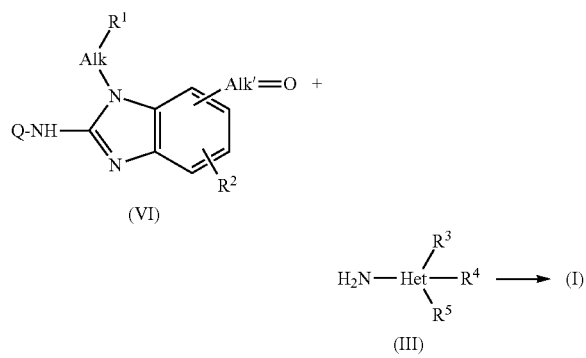

Compounds of formula (I) may be converted into each other following art-known functional group transformation reactions, comprising those described hereinafter.

Cyano groups may be reduced to aminomethylene groups, which may be alkylated. Hydroxycarbonyl groups may be esterified to $C_{1-4}$alkyloxycarbonyl groups or vice verse the latter may be hydrolysed to obtain the former.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The intermediates of formula (II-a), which are intermediates of formula (II) wherein the group Alk substituted on the phenyl part of the benzimidazole moiety is methylene, can be prepared from the corresponding hydroxymethylene substituted benzimidazoles of formula (VII) by reacting the latter with a suitable leaving group introducing agent such as a halogenating agent, e.g. $SOCl_2$, whereby the hydroxymethylene group is converted to the corresponding halomethylene group. The intermediates (VII) can be obtained from the corresponding esters (VIII) by a reduction reaction, e.g. with $LiAlH_4$. This reaction sequence is illustrated by the following schemes in which $R^a$ represents a $C_{1-6}$alkyl radical, in particular a $C_{1-4}$alkyl group which preferably is methyl or ethyl. Intermediates of formula (II) wherein Alk substituted on the phenyl part of the benzimidazole moiety is other than methylene can be obtained similarly from the corresponding intermediates (VIII) bearing a $C_{2-6}$alkyl-$COOR^a$ group.

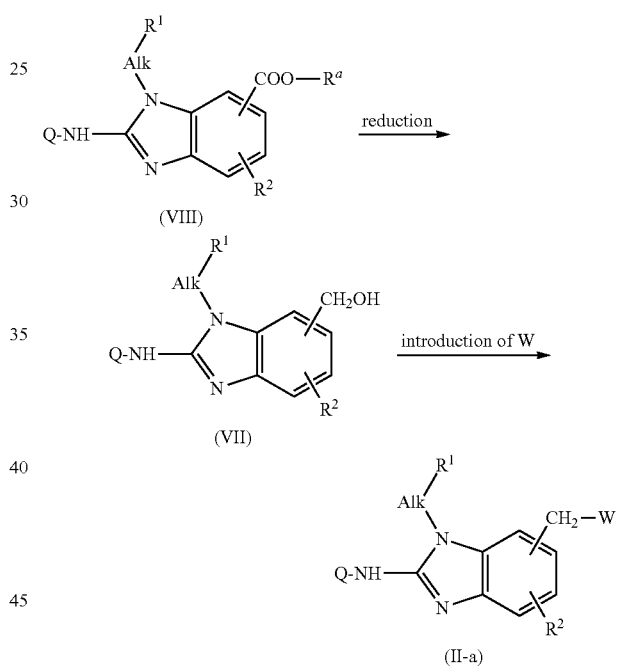

The intermediates (IV) can be obtained as outlined in the following reaction sequence.

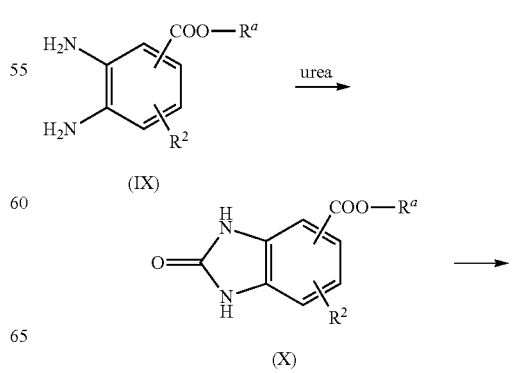

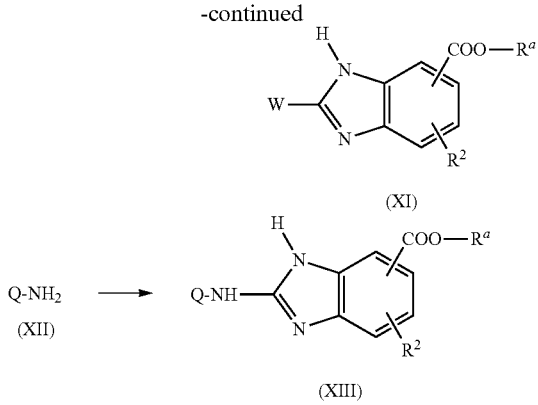

In a first step, a diaminobenzene (IX) is cyclized with urea in a suitable solvent, e.g. xylene, to yield a benzimidazolone (X). The latter is converted to a benzimidazole derivative (XI) wherein W is a leaving group as specified above, in particular by reaction of (X) with a suitable halogenating agent, for example POCl$_3$, and the resulting intermediate (XI) is reacted with the amine derivative (XII) to obtain intermediate (XIII). The latter is converted to intermediates (IV) by a reduction reaction followed by a group W-introducing reaction, following the same procedures as described above for the conversion of (VIII) to (II-a). In a final step the thus obtained products are coupled with an intermediate (III); thus obtaining the desired intermediates (IV).

The intermediates of formula (VI) can be obtained from the alcohols of formula (XIV) by an oxidation reaction with a mild oxidant, e.g. with MnO$_2$.

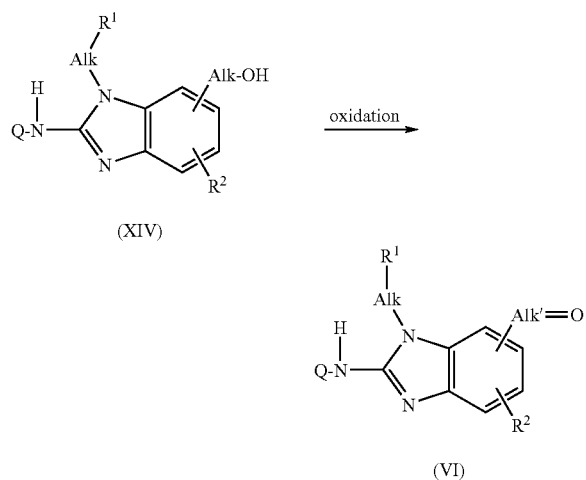

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their addition salts and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms 'compound e-1', 'compound c-3', etc. used in these examples refers to the same compounds in the tables.

The compounds were identified by LC/MS using the following equipment:

LCT: electrospray ionisation in positive mode, scanning mode from 100 to 900 amu;

Xterra MS C18 (Waters, Milford, Mass.) 5 μm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 μm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min, 100% B for 6 min to 100% A in 3 min, and equilibrate again with 100% A for 3 min).

Example 1

Scheme A

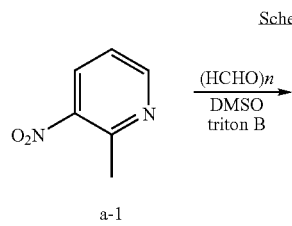

A mixture of a-1 (0.0072 mol) and paraformaldehyde (0.0058 mol) in DMSO (3.5 ml) and triton B (0.27 ml) was stirred at 90° C. for 4 hours, then cooled to room temperature and purified by column chromatography over silica gel (eluent: $CH_2Cl_2$ then $CH_2Cl_2/CH_3OH/NH_4OH$ (99/1/0.1); 15 μm). The pure fractions were collected and the solvent was evaporated, yielding: 0.3 g of intermediate a-2 (20%).

A mixture of a-2 (0.0017 mol) and Raney nickel (0.3 g) in $CH_3OH$ (30 ml) was hydrogenated at room temperature for 1 hour under 3 bar pressure, then filtered over celite. Celite was washed with $CH_3OH$. The filtrate was evaporated until dryness, yielding: 0.23 g of intermediate a-3 (93%, melting point: 168° C.).

Example 2

Scheme B

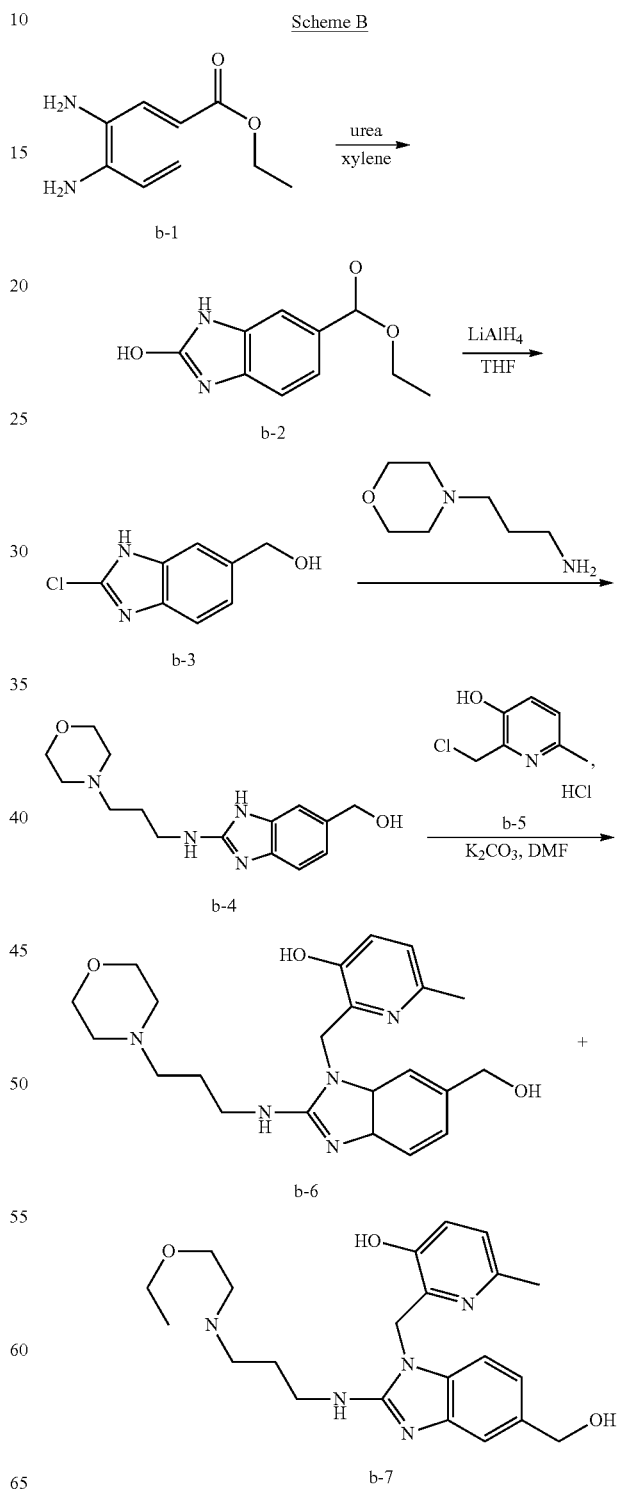

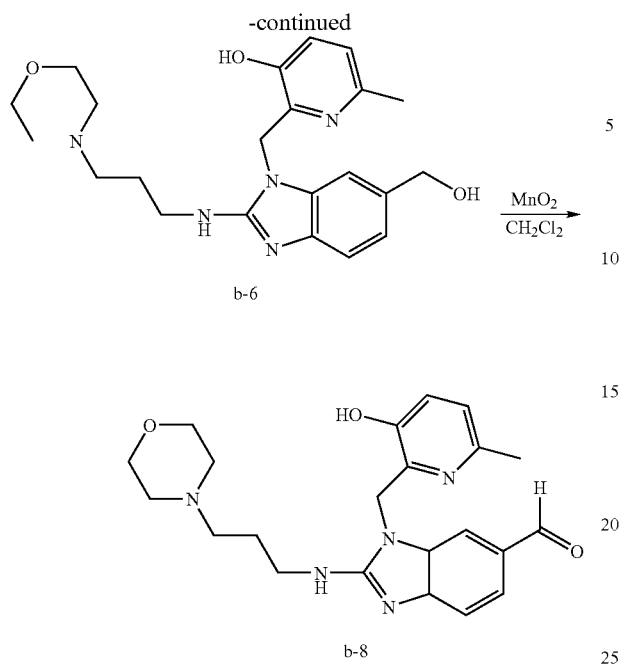

b-6

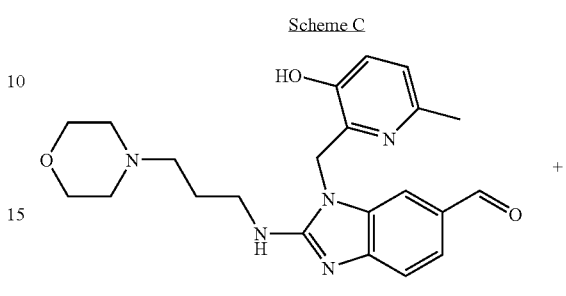

b-8

A mixture of b-1 (0.166 mol) and urea (0.199 mol) in xylene (300 ml) was stirred under reflux for 12 hours. The reaction was cooled down to room temperature. The precipitate was filtered off, rinsed with xylene and diisopropylether, and then dried, yielding: 32 g of intermediate b-2 (93%, melting point: >260° C.).

LiAlH$_4$ (0.146 mol) was added portion wise to a solution of tetrahydrofuran (200 ml) at 5° C. under N$_2$ flow. A solution of b-2 (0.073 mol) in tetrahydrofuran (200 ml) was then added drop wise. The mixture was stirred at 5° C. for 3 hours. A minimum of H$_2$O was then added, followed by a solution of CH$_2$Cl$_2$/CH$_3$OH (90/10). The resulting mixture was dried (over MgSO$_4$), filtered and the solvent was evaporated until dryness, yielding 12.6 g of intermediate b-3 (95%, melting point: 179° C.).

A mixture of b-3 (0.069 mol) and N-propylamino-morpholine (0.207 mol) was stirred at 125° C. for 4 hours, and then taken up in CH$_2$Cl$_2$/CH$_3$OH. The organic layer was washed with a 10% solution of K$_2$CO$_3$ in water, dried (over MgSO$_4$), filtered and the solvent was evaporated until dryness. The residue (37 g) was purified by column chromatography over silica gel (eluent: CH$_2$Cl$_2$/CH$_3$OH/NH$_4$OH 90/10/0.5; 20-45 μm). The pure fractions were collected and the solvent was evaporated, yielding 16.5 g of intermediate b-4 (82%).

A mixture of b-4 (0.0396 mol), b-5 (0.0475 mol) and K$_2$CO$_3$ (0.1188 mol) in dimethylformamide (110 ml) was stirred at room temperature for 12 hours. The reaction was poured into ice/water. The aqueous layer was saturated with K$_2$CO$_3$ (powder) and extracted with a solution of CH$_2$Cl$_2$/CH$_3$OH (95/5). The residue was purified by chromatography over silica gel (eluent: CH$_2$Cl$_2$/CH$_3$OH/NH$_4$OH 90/10/1; 20-45 μm). The pure fractions were collected and the solvent was evaporated, yielding 5.4 g of intermediate b-6 (33%, melting point: 192° C.) and 5 g of intermediate b-7 (31%, melting point: 134° C.).

A mixture of b-6 (0.0024 mol) and MnO$_2$ (2 g) in CH$_2$Cl$_2$ (50 ml) was stirred at room temperature for 12 hours, and then filtered over celite. Celite was washed with H$_2$O. The solvent of the filtrate was evaporated until dryness, yielding 0.9 g of intermediate b-8 (90%, melting point: 206° C.).

Example 3

Scheme C

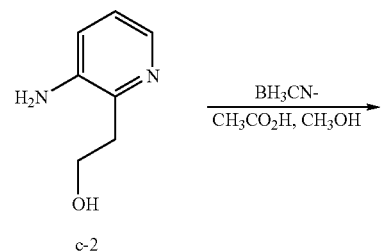

c-1

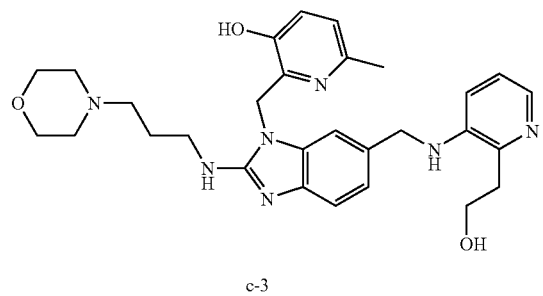

c-2

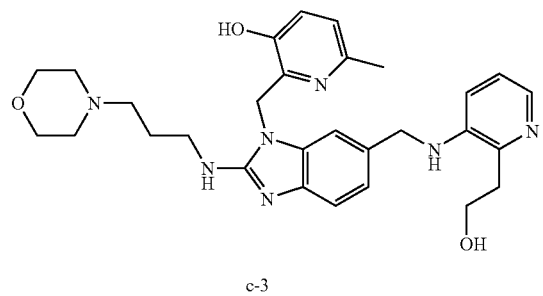

c-3

A mixture of c-1 (0.0003 mol), c-2 (0.0004 mol) and BH$_3$CN— on solid support (0.0005 mol) in CH$_3$OH (15 ml) and CH$_3$CO$_2$H (0.15 ml) was stirred at room temperature for 48 hours, then filtered, washed with CH$_3$OH and evaporated until dryness. The residue was taken up in CH$_2$Cl$_2$ and CH$_3$OH (few). The organic layer was washed with K$_2$CO$_3$ 10% in water, dried (over MgSO$_4$), filtered and the solvent was evaporated. The residue (0.19 g) was purified by column chromatography over silica gel (eluent: CH$_2$Cl$_2$/CH$_3$OH/NH$_4$OH (97/3/0.3); 3.5 μm). The pure fractions were collected and the solvent was evaporated. The residue (0.114 g, 59%) was crystallized from 2-propanone. The precipitate was filtered, washed with diisopropylether and dried. Yield: 0.1 g of final compound c-3 (51%, melting point: 211° C.).

Example 4
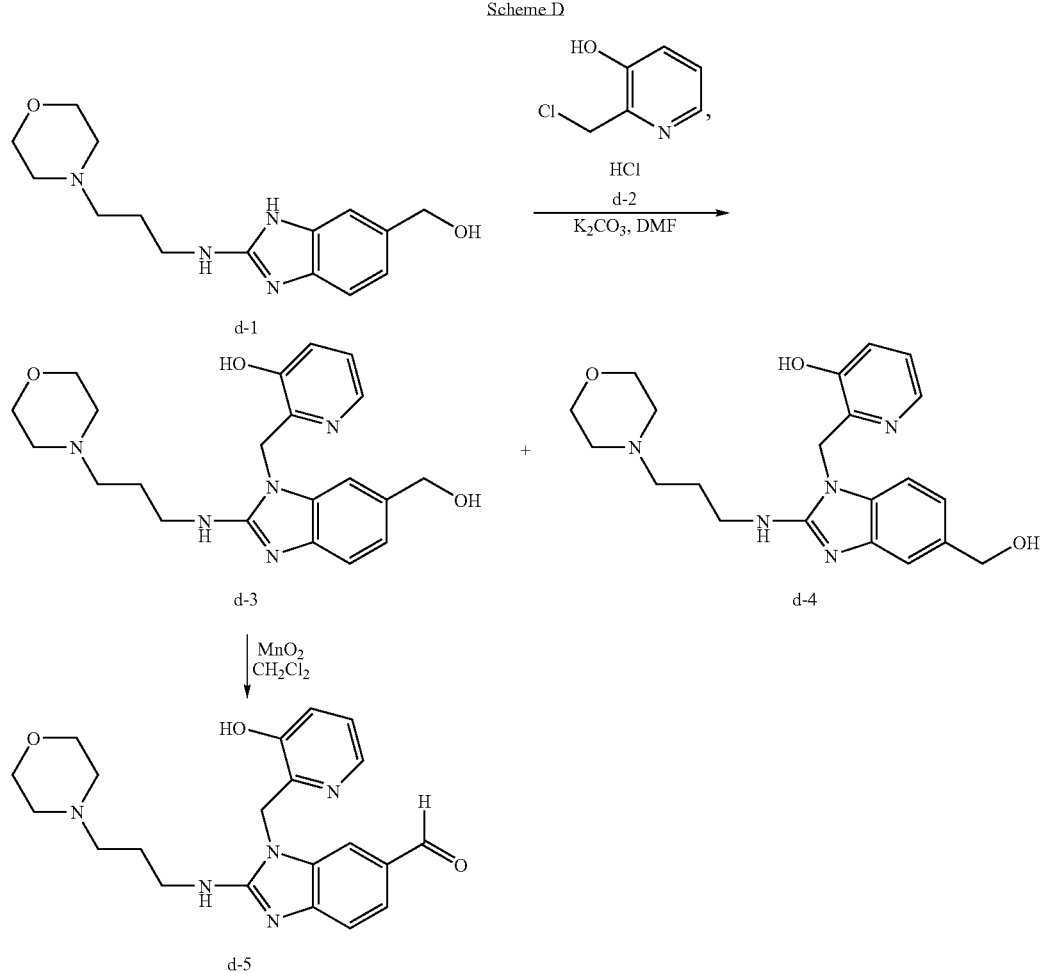
Intermediates d-3 (24%, melting point: 254° C.) and d-4 (17%, melting point: 242° C.) were synthesized according to the procedure described for intermediates b-6 and b-7.
Intermediate d-5 (80%, melting point: 208° C.) was synthesized according to the procedure described for intermediate b-8.
Example 5
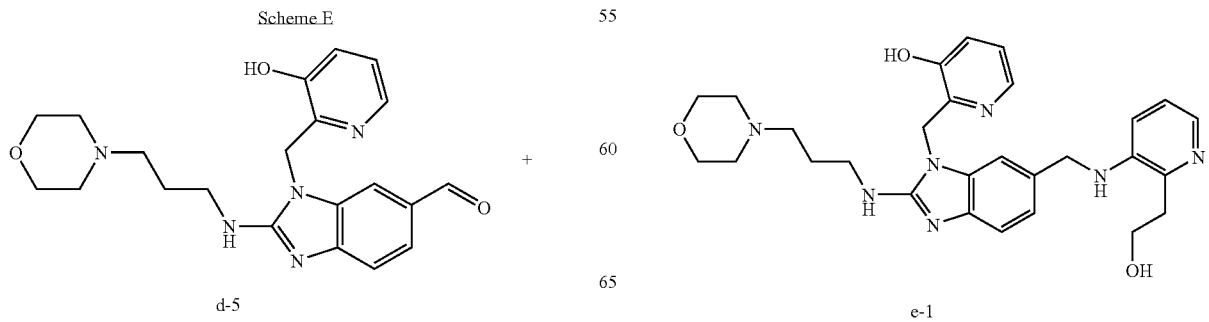
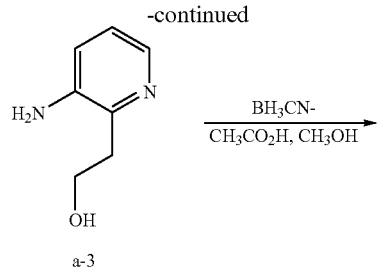

A mixture of d-5 (0.0002 mol), a-3 (0.0003 mol) and BH₃CN— on solid support (0.0003 mol) in CH₃OH (15 ml) and CH₃CO₂H (0.15 ml) was stirred at room temperature for 48 hours, then filtered, washed with CH₃OH and evaporated until dryness. The residue was taken up in CH₂Cl₂ and CH₃OH (few). The organic layer was washed with K₂CO₃ 10% in water, dried (over MgSO₄), filtered and the solvent was evaporated. The residue (0.14 g) was purified by column chromatography over silica gel (eluent: CH₂Cl₂/CH₃OH/NH₄OH (96/4/0.4); 3.5 μm). The pure fractions were collected and the solvent was evaporated. The residue (0.08 g, 62%) was crystallized from 2-propanone. The precipitate was filtered, washed with diisopropylether and dried. Yield: 0.07 g of final compound e-1 (54%, melting point: 233° C.).

Example 6

Scheme F

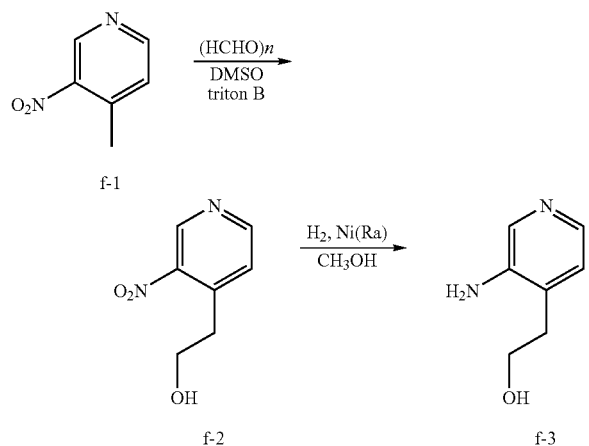

A mixture of f-1 (0.0094 mol) and paraformaldehyde (0.0075 mol) in DMSO (4.5 ml) and triton B (0.35 ml) was stirred at 90° C. for 4 hours, and then purified by column chromatography over silica gel (eluent: CH₂Cl₂; 15 μm). The pure fractions were collected and the solvent was evaporated, yielding: 0.15 g of intermediate f-2 (10%).

A mixture of f-2 (0.0008 mol) and Raney nickel (0.2 g) in CH₃OH (30 ml) was hydrogenated at room temperature for 1 hour under a 3 bar pressure, then filtered over celite. The filtrate was evaporated until dryness. Yield: 0.1 g of intermediate f-3 (82%).

Example 7

Scheme G

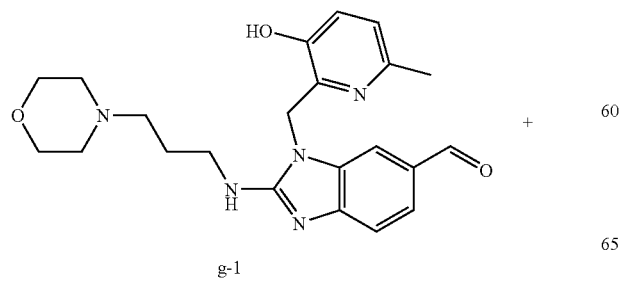

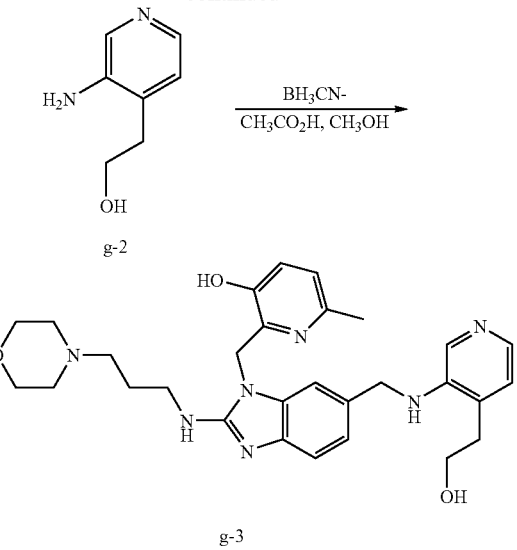

A mixture of g-1 (0.0003 mol), g-2 (0.0003 mol) and BH₃CN— on solid support (0.0004 mol) in CH₃OH (20 ml) and CH₃CO₂H (0.15 ml) was stirred at room temperature for 48 hours, then filtered, washed with CH₃OH and evaporated until dryness. The residue was taken up in CH₂Cl₂ and CH₃OH (few). The organic layer was washed with K₂CO₃ 10% in water, dried (over MgSO₄), filtered and the solvent was evaporated until dryness. The residue (0.22 g) was purified by column chromatography over silica gel (eluent: CH₂Cl₂/CH₃OH/NH₄OH (96/4/0.4); 3.5 μm). The pure fractions were collected and the solvent was evaporated. The residue (0.05 g, 31%) was crystallized from 2-propanone/diisopropylether. The precipitate was filtered off and dried. Yield: 0.043 g of final compound g-3 (27%, melting point: 207° C.).

Example 8

Scheme H

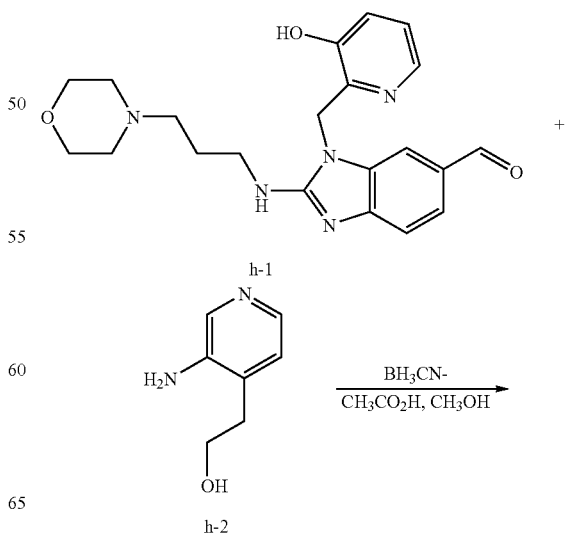

-continued

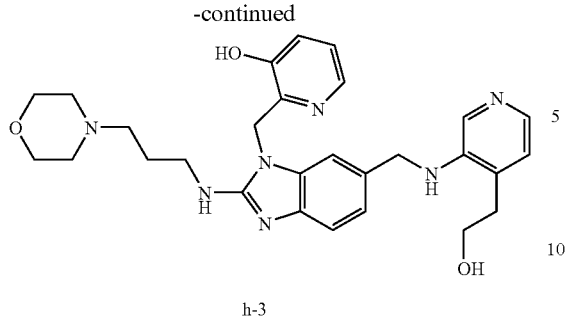

h-3

A mixture of h-1 (0.0003 mol), h-2 (0.0003 mol) and BH₃CN— on solid support (0.0004 mol) in CH₃OH (20 ml) and CH₃CO₂H (0.15 ml) was stirred at room temperature for 48 hours, then filtered, washed with CH₃OH and evaporated until dryness. The residue was taken up in CH₂Cl₂ and CH₃OH (few). The organic layer was washed with K₂CO₃ 10% in water, dried (over MgSO₄), filtered and the solvent was evaporated until dryness. The residue (0.16 g) was purified by column chromatography over silica gel (eluent: CH₂Cl₂/CH₃OH/NH₄OH 95/5/0.5; 3.5 μm). The pure fractions were collected and the solvent was evaporated. Yielding: 0.081 g (52%). This fraction was crystallized from 2-propanone/diisopropylether. The precipitate was filtered off and dried. Yield: 0.049 g of final compound h-3 (32%, melting point: 142° C.).

Example 9

Scheme I

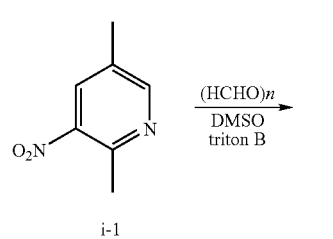

i-1

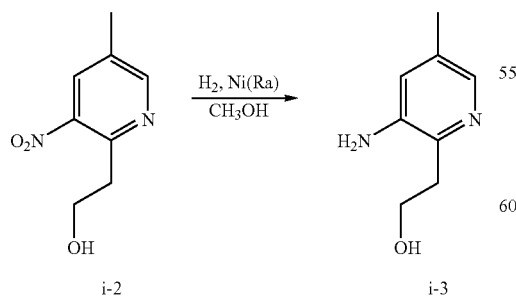

Intermediate i-2 (40%) was synthesized according to the procedure described for intermediate a-2.

Intermediate i-3 (57%, melting point: 152° C.) was synthesized according to the procedure described for intermediate a-3.

Example 10

Scheme J

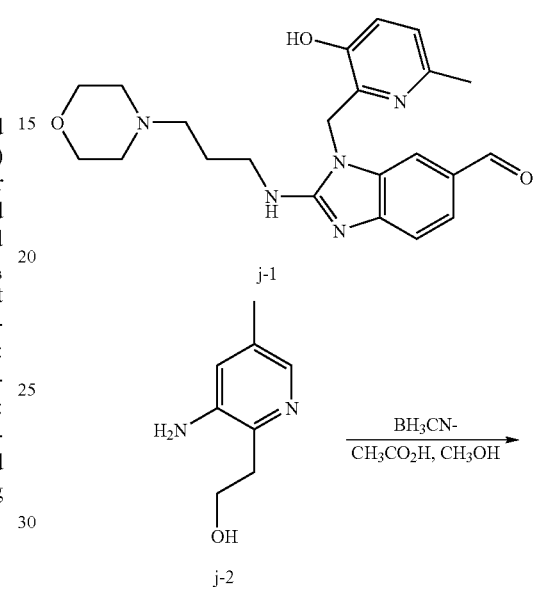

Final compound j-3 (36%, melting point: 212° C.) was synthesized according to the procedure described for intermediate c-3.

Example 11

Scheme K

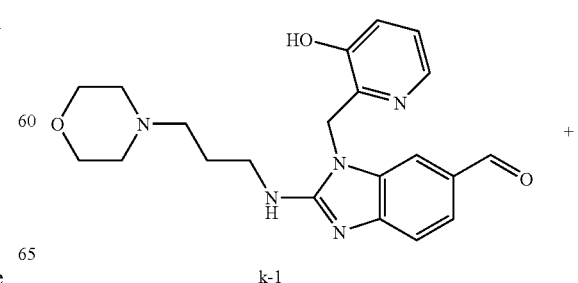

k-1

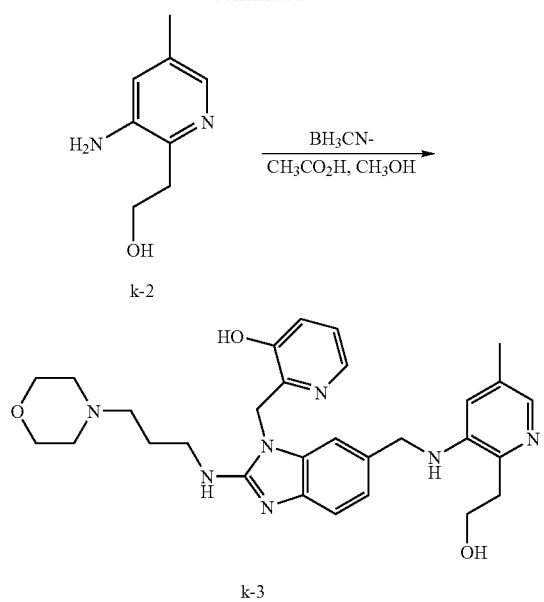

k-2

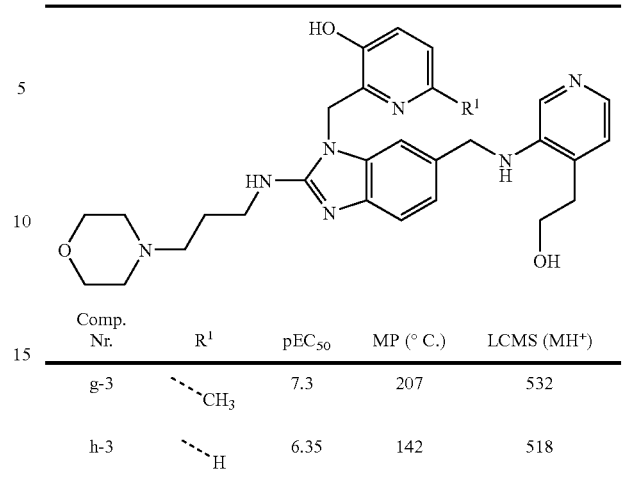

Final compound k-3 (30%, melting point: 254° C.) was synthesized according to the procedure described for intermediate e-3.

The following tables list compounds that were prepared according to any one of the above examples.

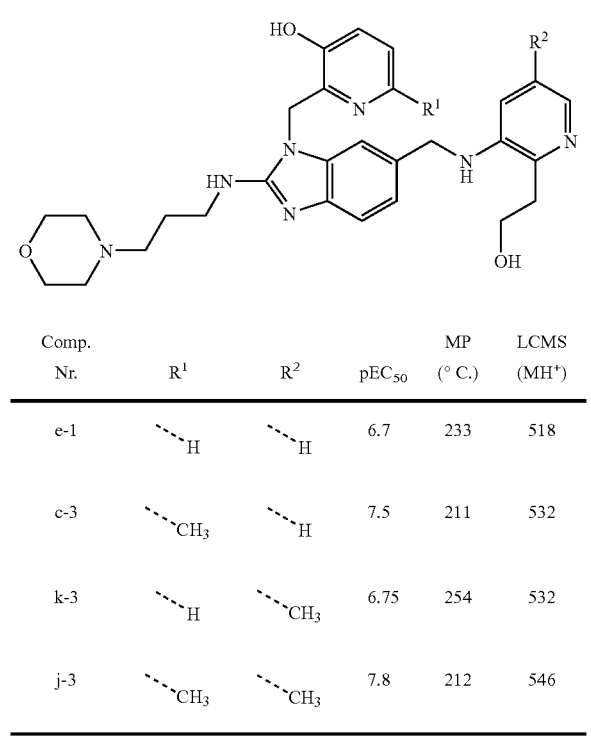

| Comp. Nr. | R¹ | R² | pEC$_{50}$ | MP (° C.) | LCMS (MH⁺) |
|---|---|---|---|---|---|
| e-1 | H | H | 6.7 | 233 | 518 |
| c-3 | CH$_3$ | H | 7.5 | 211 | 532 |
| k-3 | H | CH$_3$ | 6.75 | 254 | 532 |
| j-3 | CH$_3$ | CH$_3$ | 7.8 | 212 | 546 |

The dotted line in the above tables represents the bond by which the radical is linked to the rest of the molecule.

| Comp. Nr. | R¹ | pEC$_{50}$ | MP (° C.) | LCMS (MH⁺) |
|---|---|---|---|---|
| g-3 | CH$_3$ | 7.3 | 207 | 532 |
| h-3 | H | 6.35 | 142 | 518 |

The dotted line in the above tables represents the bond by which the radical is linked to the rest of the molecule.

Example 12

In Vitro Screening for Activity Against Respiratory Syncytial Virus

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells).

Automated tetrazolium-based colorimetric assays were used for determination of $EC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10⁵ cells/ml) of HeLa cells was added to all wells in a volume of 50 μl. The cultures were incubated at 37° C. in a 5% CO$_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and

The invention claimed is:

1. A compound of the formula

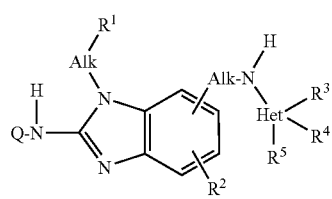

a salt or a stereochemically isomeric form thereof, wherein
Q is $C_{1-6}$alkyl substituted with morpholinyl; wherein said morphonlinyl may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-6}$alkyloxycarbonyl, aminocarbonyl, mono- or di($C_{1-6}$alkyl)aminocarbonyl, $C_{1-6}$alkylcarbonylamino, aminosulfonyl and mono- or di($C_{1-6}$alkyl)aminosulfonyl;

each Alk independently represents $C_{1-6}$alkanediyl;

$R^1$ is Ar or a heterocycle selected from pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$alkyloxy, ($C_{1-6}$alkyloxy)$C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl, aminocarbonyl, mono- and di-$C_{1-6}$alkylaminocarbonyl;

$R^2$ is hydrogen or $C_{1-6}$alkyl;

$R^3$ is hydroxy$C_{1-6}$alkyl, $C_{1-6}$alkoxy$C_{1-6}$alkyl, cyano$C_{1-6}$alkyl, aminocarbonyl-$C_{1-6}$-alkyl, mono- or di($C_{1-6}$alkyl)aminocarbonyl-$C_{1-6}$-alkyl, carboxyl-$C_{1-6}$-alkyl, $C_{1-6}$alkoxycarbonyl-$C_{1-6}$alkyl;

$R^4$ is hydrogen or $C_{1-6}$alkyl;

$R^5$ is hydrogen or $C_{1-6}$alkyl;

Ar is phenyl or phenyl substituted with 1 to 5, such as 1, 2, 3 or 4, substituents selected from halo, hydroxy, amino, mono- or di($C_{1-6}$alkyl)amino, $C_{1-6}$alkylcarbonylamino, $C_{1-6}$alkylsulfonylamino, cyano, $C_{1-6}$alkyl, $C_{2-6}$alkenyl, $C_{2-6}$alkynyl, phenyl, hydroxy$C_{1-6}$alkyl, polyhalo$C_{1-6}$alkyl, amino$C_{1-6}$alkyl, mono- or di($C_{1-6}$alkyl)amino$C_{1-6}$ alkyl, $C_{1-6}$alkyloxy, polyhalo$C_{1-6}$alkyloxy, phenoxy, aminocarbonyl, mono- or di($C_{1-6}$alkyl)aminocarbonyl, hydroxycarbonyl, $C_{1-6}$alkoxycarbonyl, $C_{1-6}$alkylcarbonyl, aminosulfonyl, mono- and di($C_{1-6}$alkyl)aminosulfonyl;

Het is a heterocycle selected from the group consisting of pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl.

2. A compound according to claim 1 wherein the compound has the formula (I-a):

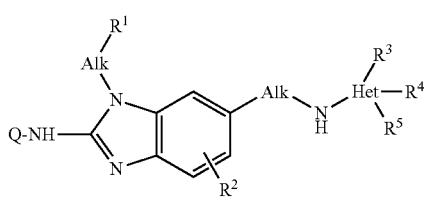

wherein Q, $R^1$, each Alk, $R^2$, $R^3$, $R^4$ and $R^5$ are as claimed in claim 1.

3. A compound according to claim 1 wherein $R^1$ is pyridyl substituted with 1 or 2 substituents independently selected from the group consisting of hydroxy, $C_{1-6}$alkyl, halo, $C_{1-6}$alkyloxy, and ($C_{1-6}$alkyloxy)$C_{1-6}$alkyloxy.

4. A compound according to claim 1, wherein each Alk is methylene.

5. A compound according to claim 1, wherein $R^2$ is hydrogen.

6. A compound according to claim 1, wherein $R^3$ is hydroxy$C_{1-6}$alkyl, $C_{1-6}$alkoxy$C_{1-6}$alkyl or cyano$C_{1-6}$alkyl.

7. A compound according to claim 1, wherein $R^4$ is hydrogen.

8. A compound according to claim 1, wherein $R^5$ is hydrogen.

9. A compound according to claim 1, wherein Het is pyridyl.

10. A compound according to claim 1, wherein Q is $C_{1-6}$alkyl substituted with morpholinyl.

11. A pharmaceutical composition comprising a carrier and as active ingredient a compound as defined in claim 1.

12. A pharmaceutical composition made by mixing a compound of claim 1 and a pharmaceutically acceptable carrier.

13. A process for making a pharmaceutical composition comprising mixing a compound of claim 1 and a pharmaceutically acceptable carrier.

14. The pharmaceutical composition of claim 11, further comprising an antiviral agent.

15. The pharmaceutical composition of claim 14, further comprising an antiviral agent selected from the group consisting of interferon-beta and tumor necrosis factor-alpha.

* * * * *